United States Patent [19]

Schneider

[11] Patent Number: 4,933,187
[45] Date of Patent: Jun. 12, 1990

[54] CHEMICAL PELLETS FOR AQUATIC ATTACK PROTECTION BELT

[76] Inventor: David P. Schneider, 4 Woodside Dr. East, Apalachin, N.Y. 13732

[21] Appl. No.: 394,818

[22] Filed: Aug. 17, 1989

Related U.S. Application Data

[63] Continuation-in-part of Ser. No. 199,468, May 27, 1988.

[51] Int. Cl.$^5$ ............................................. A61K 9/14
[52] U.S. Cl. .................................. 424/497; 424/490; 424/462
[58] Field of Search ............... 424/405, 411, 611, 408, 424/410, 709, 501, DIG. 9–DIG. 10, 497; 514/918, 919, 920, 965; 428/402, 407

[56] References Cited

U.S. PATENT DOCUMENTS

| | | | |
|---|---|---|---|
| 4,000,093 | 12/1976 | Nicol et al. | 252/550 |
| 4,391,724 | 7/1983 | Bacon | 252/550 |
| 4,602,384 | 7/1986 | Schneider | 428/907 |
| 4,820,449 | 4/1989 | Menke et al. | 252/550 |

FOREIGN PATENT DOCUMENTS 568673  4/1945  United Kingdom ................ 424/709

*Primary Examiner*—Thurman K. Page
*Assistant Examiner*—James M. Spear
*Attorney, Agent, or Firm*—Keith T. Bleuer

[57] ABSTRACT

A belt including a pair of opposite layers of sheet material and subdivided into a series of pockets for receiving pellets of shark-repulsive chemical. One of the pellets is untreated so as to dissolve in water relatively quickly, another of the pellets is impregnated with water soluble glue, another of the pellets is coated with the glue while a fourth of the pellets is coated with epoxy for preventing water application to the chemical of the pellet until the pellet is manually broken.

2 Claims, 2 Drawing Sheets

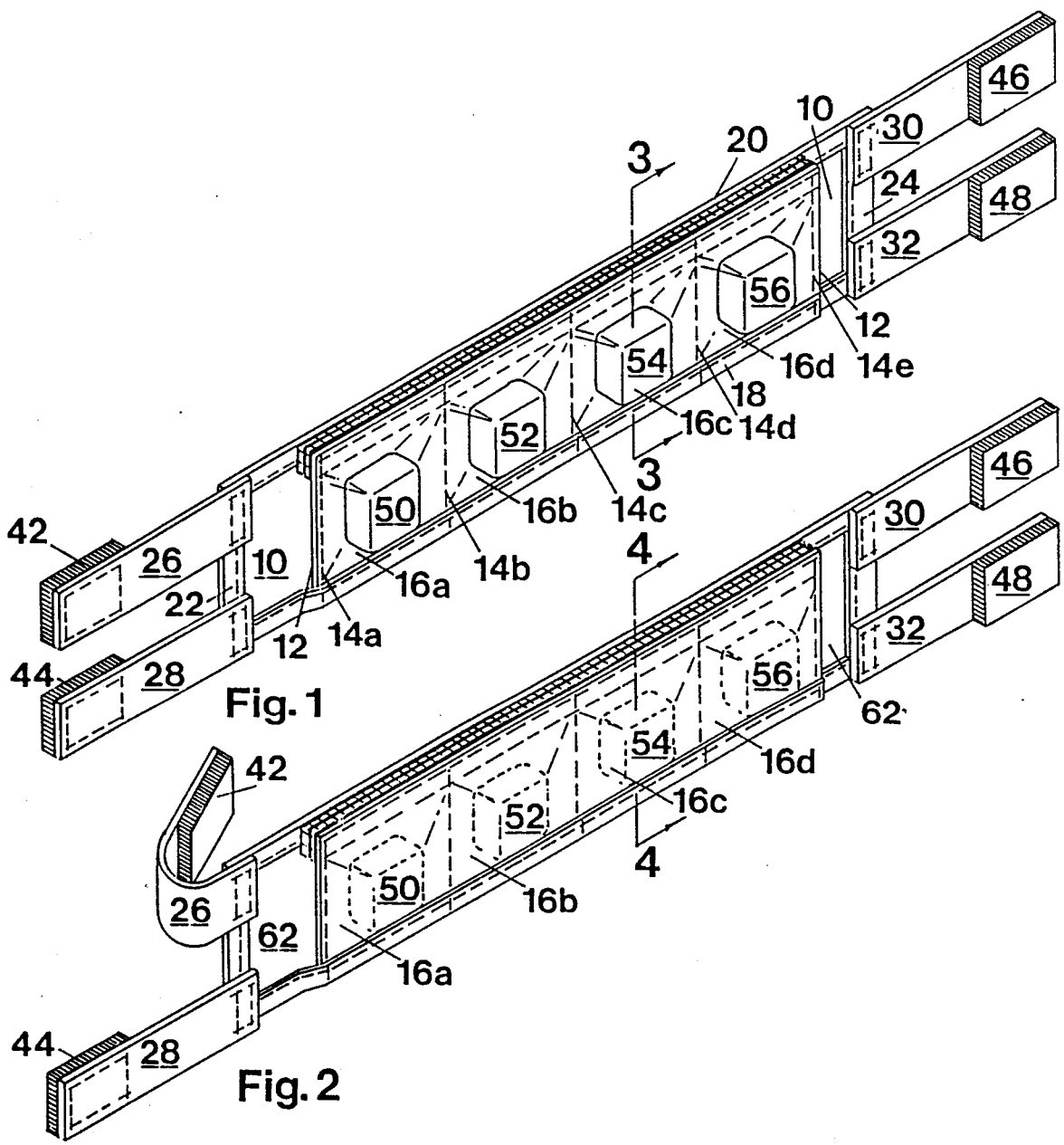

White Pellet

Red Pellet

CHEMICAL PELLETS FOR AQUATIC ATTACK PROTECTION BELT

This application is a continuation-in-part of my prior, copending application, Ser. No.. 07/199,468, filed May 27, 1988 for "Aquatic Attack Protection Belt and Chemical Pellets Therefor."

BACKGROUND OF THE INVENTION

The invention relates to wearing apparel for humans having built in receptacles for containing chemicals that will protect a person from attacks of fish, such as sharks, in the water; and more particularly the invention relates to such wearing apparel in the form of belts that may be used about the waist of the wearer or about his wrists or ankles. Shark attack has long been recognized as a serious problem, and many solutions have been proposed. One of the proposed solutions is to provide antishark suits formed of steel mesh, but such a suit is quite heavy and is correspondingly unmanageable.

The invention is a general improvement on that disclosed in my U.S. Pat. No. 4,602,384 issued July 29, 1986 disclosing a shark protection suit, while the present invention in particular is to improved belts for wearer use.

SUMMARY OF THE INVENTION

It is an object of the present invention to provide improved anti-shark pieces of wearing apparel, particularly belts that may be worn about the waist, the wrists or the ankles of the user having built in receptacles for shark repelling chemicals dissolvable in sea water, particularly those in pellet form. The belts preferably have water transmitting fabric forming one side of each of the receptacles so that sea water may enter the receptacles for dissolving the chemical therein.

It is also an object of the present invention to provide reduced and controlled dissolving rates of the pellets for prolonging the duration of protection against all sharks. In this connection, it is an object to coat such pellets with a water soluble glue which must first dissolve before the sea water is effective on the pellet itself. It is also an object to provide a form of the pellet which is coated with an epoxy or other water impervious material so that the pellet must be broken manually or by the fish before the sea water can be effective on the interior of the pellet.

BRIEF DESCRIPTION OF THE DRAWINGS

FIG. 1 is an isometric view of a shark repellent belt having a series of pockets holding pellets of shark repellent chemical;

FIG. 2 is an isometric view of a belt constituting a modification of the invention;

DESCRIPTION OF THE PREFERRED EMBODIMENTS

Figure 3:
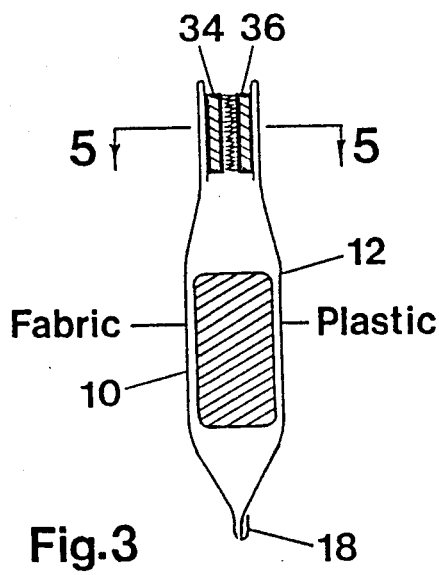
FIG. 3 is a sectional view on an enlarged scale taken on line 3—3 of FIG. 1.
Figure 4:
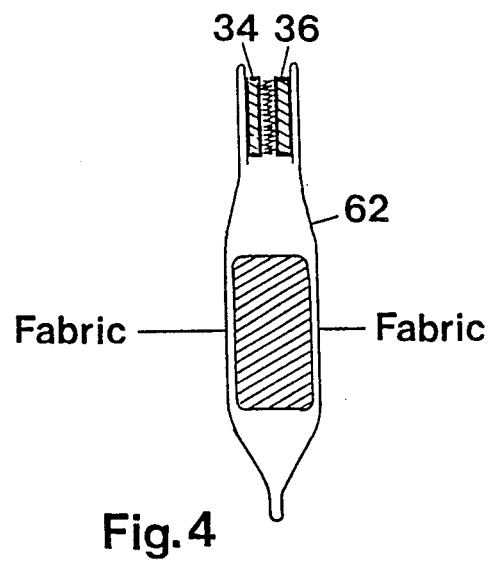
FIG. 4 is a sectional view on an enlarged scale taken on line 4—4 of FIG. 2.

Referring to FIG. 1, the belt therein illustrated comprises a thin sheet fabric layer strip 10 and a layer strip 12 of thin transparent plastic sheet. The layers 10 and 12 are stitched together on vertical lines 14a, 14b, 14c, 14d and 14e to form receptacles or pockets 16a, 16b, 16c and 16d. Hems 18 and 20 are formed respectively on the lower and upper edges of the fabric 10, and the fabric 10 is provided with hems 22 and 24 on its ends. The hem 18 overlaps the plastic layer 12 as seen in FIG. 3 and is stitched to the transparent layer 12 for forming the bottoms of the pockets 16a–16d. Cloth strips or tapes 26 and 28 are stitched to the hem 22 and cloth strips or tapes 30 and 32 are stitched to the hem 24 as shown in FIG. 1 and serve to complete the belt as will be described.

Figure 5:
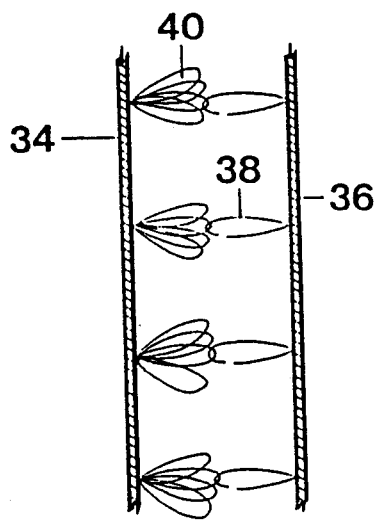
FIG. 5 is a sectional view on an enlarged scale taken on line 5—5 of FIG. 3.
Figure 6:
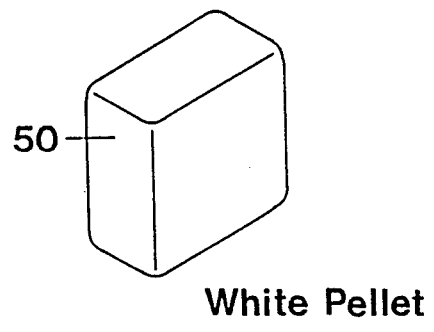
FIG. 6 is an isometric view of one of the pellets of shark repellent chemical which in this case is a "white" pellet.

Flexible fabric strips 34 and 36 (see FIG. 5) constituting a separable fastening device are stitched respectively to the layers 10 and 12 at their upper edges on opposite parallel extending terminal portions of the layers 10 and 12 as shown particularly in FIG. 2 so that the strips 34 and 36 are located opposite each other and may contact each other when the layers 10 and 12 are pressed together on their upper edges whereby to selectively close the pockets 16a–16d. The separable fastening device comprising the strips 34 and 36 is preferably of the type on the market labeled "Velcro" ® and is covered by U.S. Pat. Nos. 3,083,737, 3,009,235, 3,147,528, 3,154,837 and others. The separable fastening device as shown in FIG. 5 is particularly that shown in U.S. Pat. No. 3,009,235 and includes a very large number of closely spaced engagable hooking elements 38 and 40 comprising respectively hooks and loops all of flexible resilient material. The strips 34 and 36 constitute bases of sheet material and the hooking elements 38 and 40 each extends generally normally from one surface of the base to which they are secured. The number of loops 40 per unit area of the strips 34 and 36 is substantially greater than the number of hooks 38 per unit area so that, when the strips 34 and 36 are pressed toward one another in face to face relation, a very large number of the hooks 38 will engage a very large number of the loops 40 to secure the strips 34 and 36 in face to face relation. Since the hooks 38 and loops 40 are of resilient material, the fabric strips 34 and 36 may easily be separated by pulling them apart manually so as to open the upper ends of the pockets 16a–16d. Oblong pads 42, 44, 46 and 48 of such "Velcro" ® material are respectively stitched onto the ends of the fabric strips 26, 28, 30 and 32 as shown so that, when the belt is bent in the form of a circle, the pads 42 and 46 and the pads 44 and 48 may engage and hold the belt in this form.

Cubes or pellets 50, 52, 54 and 56 are disposed respectively in the pockets 16a–16d. These pellets are basically the same except that the pellet 52 is impregnated with a water soluble glue; the pellet 54 is also impregnated with the glue but in addition has a coating 58 on its exterior surface of the glue; and the pellet 56 is of the same type as the pellet 54 but is in addition provided with a red coating 60 (see FIG. 8) for purposes to be described. The pellet 50 is the basic type and is made of a dry, granular anhydrous sodium sulfate and liquid sodium lauryl sulfate mixed together in equal parts by volume and dried so that the pellet 50 when so formed retains its cube form in the pocket 16a rather than spreading into granular particles. Such chemical cubes so formed can also accept the addition of varying amounts of polyvinyl acetate resin latex (commonly known as organic, water soluble, white liquid glue) which adds the effect of prolonging the time for a given volume of the mixture to dissolve into water when the cubes made from it are immersed in water. The pellet 52 is of the latter type in which the chemicals are mixed together with the white liquid glue being an additional component of the mixture. In order to form the pellet 52, the normal amount of liquid white glue to add is one part by volume to every two parts of liquid sodium lauryl sulfate by volume, although 50% more or less glue by volume may be used to vary the time required to dissolve the cube.

The pellet 54 is identical with the pellet 52 except that in addition to containing the white liquid glue as a component, it also has a coating 58 of this glue so as to further delay the dissolving rate of the cube.

Figure 7:
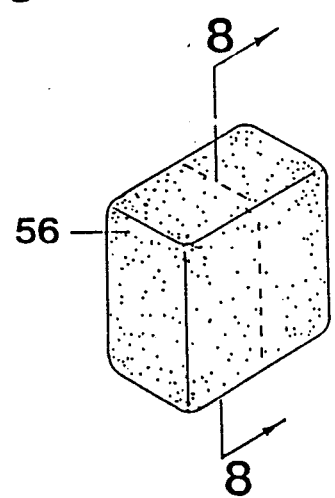
FIG. 7 is an isometric view of another of the pellets which in this case is a "red" pellet.
Figure 8:
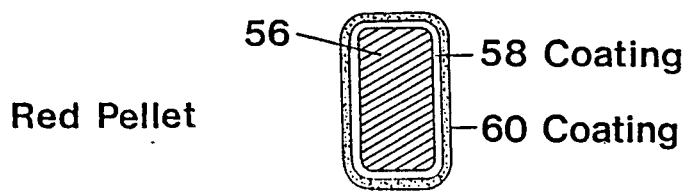
FIG. 8 is a sectional view taken on line 8—8 of FIG. 7.

The pellets 50, 52 and 54 are usually white, while the pellet 56 is usually red in color. The pellet 56 is shown in FIGS. 7 and 8 and will be observed to have the first coating 58 and the second coating 60. The first coating 58 is of the white glue previously mentioned, and the second coating 60 is a coating of waterproof epoxy having permanent red ink mixed with the coating, this ink being of the same type as used in writing pens.

The layer 10 is of a water penetratable cloth such as sailcloth. The layer 12 is made from a see-through plastic sheet so that the user can visually confirm the presence of pellets 50, 52, 54 and 56 in the receptacles 16a, 16b, 16c and 16d. The plastic can be low density polyethylene of approximately 0.003 inch in thickness but can vary in type of plastic and thickness and even somewhat in its transparency. The plastic sheet 12 should be such that it is flexible enough to serve comfortably as a human garment and allow standard sewing techniques to be used to join it to the layer 10. The cubes 50, 52, 54 and 56 are formed from the chemicals above mentioned which are in a granular or liquid form and are dried at room temperature after the mixing of the chemicals and along with the coatings 58 and 60 when used so that they retain their dried shape.

In usage, the belt as shown in FIG. 1 is bent around the waist of the user, and the pads 42 and 46 and the pads 44 and 48 are brought together so as to cause the flexible hooking elements 38 and 40 of the pads to interengage to hold the belt about the user. More or less of the lengths of the pads 42, 44, 46 and 48 may be utilized in this manner to adjust the length of the belt to various waist sizes. Other fastening devices in lieu of these pads may be used, such as metal rings through which the strips 26, 28, 30 and 32 extend and are tied or the strips 26, 28, 30 and 32 may be used without these pads or rings and may simply be tied together for holding the belt in place on the user.

When the belt is immersed with the user in sea water, the fabric layer 10 forming one side of each of the pockets 16a–16d allows water passage to occur through layer 10 into each of these pockets. The cube 50 dissolves slowly into and through the pocket 16a and fabric layer 10 out into the sea water in which the human wearing the belt is immersed to form an aura of chemically treated and polluted water about the belt and its user. The presence of this dissolved chemical in the water offends all types of sharks to the extent that they refuse to stay any time at all in the vicinity of the person wearing the belt to thus protect the user.

The cube 52 likewise dissolves into the sea water about the person wearing the belt but at a lower rate than the cube 50 due to the glue mixed in the cube 52. This thus prolongs the time for a given volume of the sodium lauryl sulfate mixture to dissolve into the water and prolongs the time of protection for the human wearing the belt. The cube 52 is of the same composition as the cube 50 but has the white liquid water soluble glue as a component of the mixture as described. The cube 54 functions in the same manner as the cubes 50 and 52 but prolongs the overall time of protection for the user, since the glue coating 58 on the cube 54 must first dissolve before the sodium lauryl sulfate interior of the cube 54 has water applied to it and dissolves. The red colored epoxy coating 60 on the cube 56 isolates the interior of the cube 56 from water and from dissolving until the cube 56 is manually bent enough to make the hard epoxy coating snap open to reveal the interior of the cube, and the red coloring is to show a user that this cube is waterproof and must be broken open before it will dissolve. The red cube 56 of course is visible through the transparent layer 12 to the user for this purpose. Needless to say, if a shark moves sufficiently close to the FIG. 1 belt as worn by the user and bites into any of the cubes 50, 52, 54 and 56, the sea water instantly dissolves the sodium lauryl sulfate to pollute the water with this chemical and immediately drives the fish away. Since the cube 56 is coated with epoxy (or other waterproof coating material as will be described), this cube may be submerged for an indefinite time along with others of the same type.

Although the FIG. 1 belt has been described for usage by a human, it may be also effective for protecting nautical hardware and for this purpose is simply wrapped around the hardware. For this usage, it may be desirable to use many of the cubes 56 protected by the epoxy or other waterproof coating 60 and to rely on a bite by a shark to open the chemical contents to melting for protection for an extended period of time.

The belt shown in FIG. 2 is the same as the belt shown in FIG. 1 except that a layer 62 of fabric is substituted for the transparent layer 12. The layer 62 is integral with the layer 10 so that the water penetratable cloth forms both sides of each of the pockets 16a–16d to increase the speed at which the water attacks the cubes. As another use, these belts could be made of materially shorter lengths so as to fit about the ankles or wrists of the user. In this case, fewer than four pellet receiving pockets 16 could be provided, and any or only some of the pellets 50, 52, 54 and 56 could be used.

Other variations are also possible within the purview of the invention. For example, instead of a red dye for the cube 56, a purple dye or a green dye could be used and would indicate when the cube is broken, since the white interior of the cube only then would be visible through the transparent layer 12. Other types of melting inhibitors and controllers could also be used instead of the water soluble white glue. Starch for example could be used, and the thickness of the coating 58 could also be varied to change the time at which the sea water reaches the interior of the cube 54. The water inhibiting epoxy coating 60 could also be of another type of water inhibitor, such as for example waterproof varnish or anti-fouling waterproof paint of the type commonly used for boat bottoms which would prevent the buildup of marine organisms that might retard dissolving of the pellets after prolonged contact with sea water. As another variation, the water penetratable sailcloth for the cloth 10 and 62 could be replaced by a water impenetratable cloth which would allow the belt to be used on nautical hardware and would be effective only when the shark bites through the belt and into one of the chemical cubes. Such a construction would assure that the cubes are effective for a much longer time than if the sea water is continuously in contact with the cubes. The horizontal tapes 26, 28, 30 and 32 are illustrated to hold the belts in place; and it will be obvious that one or more vertical tapes fastened along the lengths of the belts could be added for holding the belts on a piece of unusually shaped nautical hardware for example.

It is thus apparent that there are two chemical compositions for the cubes. One for the cube 50 is fast melting and consists of only sodium lauryl sulfate and sodium sulfate while the second has these two chemicals mixed also with the white glue for retarding the melting effect. It will also be apparent that there are two types of coatings, the white glue on the pellet 54 and the epoxy or other waterproof coating on the pellet 56. These coatings may be used interchangeably, but the glue coating 58 beneath the epoxy coating 60 has a singular purpose of preventing the epoxy from penetrating into the porous chemical of which the pellet is formed thereby creating too thick a coating for a human to break once the coatings are cured and hard. If only the white glue is used as a coating, it is much easier to break even though it soaks into the surface of the cube formed of the two chemicals above mentioned either with or without the glue as a component of the mixture. However for pellets to be used on marine hardware just the epoxy coating without an interior coating 58 of glue would be sufficient, since a human will not have to break one of these pellets open; a shark would be more than sufficient to accomplish this. It will be apparent that if desired, the colored ink could be mixed with the white glue used as a coating for helping a person to recognize the different types of pellets. Although the pellets are shown as cubes, it will be apparent that the pellets could as well have other shapes, such as disc or star-shaped. The pellets could also, instead of being dried at room temperature, be dried using an ultra violet cure for example; and it may be noted that the pellets after drying retain their shape even without the use of any glue at all or the use of any coatings. All of the pellets of all of the types disclosed have infinite shelf life if not immersed in water.

It may be noted that either of the belts of FIG. 1 or FIG. 2 may, instead of being worn above the waist, could be worn like a bandoleer of cartridges — that is, over one shoulder and underneath the opposite arm of the user and crossing the chest. This would keep a certain portion of the pockets 16a-16d mostly out of the water, and therefore the chemicals in these pockets would not melt as fast in those pockets by or beside the user's head. After a day or so, when the submerged pockets are empty, the user could rotate the belt so the pockets which had been beside the user's head could now be submerged to dissolve the pellets therein. This would prolong even further the protection provided by the belt.

It is thus apparent that I have disclosed a relatively fast melting pellet 50 with only the two basic chemicals as constituents, a slower melting pellet 52 with the white glue as a component of the mixture, a still slower melting pellet 54 with a white glue coating and the fourth pellet 56 which is not affected by being submerged in water until the pellet is broken open by manual effort or by an attacking shark.

The sodium lauryl sulfate above mentioned is the chemical or surfactant in the pellets 50, 52, 54 and 56 that offends the sharks when the pellets dissolve in sea water. Possible substitute chemicals or surfactants are sodium dodecal sulfate, sodium octyl sulfate and sodium octyl/decyl sulfate, all members of a family called alkyl sulfate surfactants. Another substitutable family of surfactants or chemicals and effective for offending sharks when dissolved are the nonionic hydrocarbon surfactants.

White glue has been mentioned to delay the melting of the slower melting pellets, and this glue may be replaced by common gelatin of the type used in medicine capsules. For this purpose, water soluble waxes may also be used.

The pellets may be formed in any suitable manner. For example, the chemicals of the pellets may be emulsified into a glycerine base and formed into the pellets, and these may be other than equal in dimensions on all edges and may be in the form of an ordinary bar of soap, for example, which has one long dimension in comparison to the others. Also, the pellets may be formed in the form of a shark, for example, which would alert users not to use the pellets as bars of soap. Distinctive coloring may also be added to the chemicals of the pellets if desired. Also, initially, the chemicals for the pellets may come in the form of flakes or liquid.

Using sodium sulfate and sodium lauryl sulfate for the pellets, as first mentioned, 10% by volume of white glue may be used for helping to stabilize the pellets in cake form.

I claim:
1. A pellet formed of granular anhydrous sodium sulfate, liquid sodium lauryl sulfate, a water soluble white liquid glue comprised of polyvinyl acetate, for retarding the dissolution of the pellet in water, coated with an epoxy coating, which effectively shields the interior of the pellet until the pellet is broken.

2. A pellet as set forth in claim 1 and including water soluble white liquid glue with which the pellet is impregnated for the purpose of retarding the dissolution of the pellet in water, the amount of the glue being about 10% by volume of the pellet.

* * * * *